US 8,708,186 B2

(12) United States Patent
Lepot

(10) Patent No.: US 8,708,186 B2
(45) Date of Patent: Apr. 29, 2014

(54) BOX FOR STORING, PROTECTING, AND TRANSPORTING CONTAINERS

(75) Inventor: Eric Lepot, Louvain-la-Neuve (BE)

(73) Assignee: Flexiways S.P.R.L., Louvain-la-Neuve (BE)

( * ) Notice: Subject to any disclaimer, the term of this patent is extended or adjusted under 35 U.S.C. 154(b) by 205 days.

(21) Appl. No.: 13/265,359

(22) PCT Filed: Apr. 22, 2010

(86) PCT No.: PCT/EP2010/055399
§ 371 (c)(1),
(2), (4) Date: Oct. 20, 2011

(87) PCT Pub. No.: WO2010/122129
PCT Pub. Date: Oct. 28, 2010

(65) Prior Publication Data
US 2012/0045311 A1   Feb. 23, 2012

(30) Foreign Application Priority Data
Apr. 22, 2009   (BE) .................................. 2009/0249

(51) Int. Cl.
*B65D 77/20* (2006.01)
*B65D 77/10* (2006.01)
*B65D 1/46* (2006.01)
*B65D 1/40* (2006.01)

(52) U.S. Cl.
USPC ........... 220/655; 220/508; 220/519; 220/657; D7/629; D9/425

(58) Field of Classification Search
USPC ................. 206/216, 386, 518, 557, 571, 585; 220/652; D9/425
See application file for complete search history.

(56) References Cited

U.S. PATENT DOCUMENTS

| 3,351,265 | A | * | 11/1967 | Miller ....................... 229/125.33 |
| 3,749,276 | A | * | 7/1973 | Davis ............................. 220/789 |
| D277,993 | S | * | 3/1985 | Sinchok ......................... D3/312 |

(Continued)

FOREIGN PATENT DOCUMENTS

| DE | 298 14 026 U1 | 11/1998 |
| DE | 299 10 076 U1 | 9/1999 |

(Continued)

OTHER PUBLICATIONS

English language Abstract for WO 99/45985.

(Continued)

*Primary Examiner* — Gregory Adams
(74) *Attorney, Agent, or Firm* — Christopher Casieri

(57) ABSTRACT

The present invention relates to a box (10) for storing, transporting, and protecting vertically suspended containers with an upper opening (11), a rectangular bottom (12), lower side walls (13) connected to said bottom (12), and a step (14) connected to said lower side walls (13) and forming a bearing for supporting a plate (15). Said box (10) includes upper side walls (16) connected to said step (14), and each comprises at least one portion (17; 43) extending to the end of the box, each of said upper side walls also being connected to an upper edge (22) extending outside the box. An edge (20) is positioned on the upper corners (21) of said box (10). The present invention also relates to a container for transporting such boxes and to a method for palletizing and depalletizing said boxes.

18 Claims, 7 Drawing Sheets

(56) References Cited

U.S. PATENT DOCUMENTS

| | | | |
|---|---|---|---|
| 4,548,824 A | | 10/1985 | Mitchell |
| 4,660,734 A | * | 4/1987 | Heaney et al. ............... 220/657 |
| D302,774 S | * | 8/1989 | Murphy ......................... D7/629 |
| 4,944,730 A | | 7/1990 | Plucinski |
| 4,967,908 A | * | 11/1990 | Kessler ......................... 206/518 |
| 5,029,725 A | * | 7/1991 | Roth ............................. 220/655 |
| D363,662 S | * | 10/1995 | Plater ........................... D9/425 |
| 6,012,595 A | | 1/2000 | Thilly |
| D472,773 S | * | 4/2003 | Samartgis ..................... D7/629 |
| 2004/0262322 A1 | * | 12/2004 | Middleton et al. ............ 220/675 |

FOREIGN PATENT DOCUMENTS

| | | |
|---|---|---|
| DE | 20 2007 005651 U1 | 8/2007 |
| DE | 10 2007 028009 A1 | 12/2008 |
| EP | 1 088 566 A | 4/2001 |
| EP | 1088566 A1 * | 4/2001 |
| WO | WO 99/45985 A | 9/1999 |

OTHER PUBLICATIONS

English language Abstract for EP 1 088 566.
English language Abstract for DE 10 2007 028009.

* cited by examiner

BOX FOR STORING, PROTECTING, AND TRANSPORTING CONTAINERS

This application is a 371 application of PCT/EP2010/055399, filed Apr. 22, 2010, which, in turn, claims priority of Belgian Patent Application No.: BE2009/0249, filed on Apr. 22, 2009.

SUBJECT OF THE INVENTION

The present invention relates to a box for storing, transporting and protecting containers. The invention relates, more particularly, to a box for storing, protecting and transporting vertically-suspended containers such as, for example, containers of medical products. The invention also relates to a container for transporting said boxes, an automatic palletization and depalletization method and a use of the boxes.

TECHNOLOGICAL BACKGROUND

Currently, the containers of medical products, such as glass syringes, are packaged by the manufacturers in a so-called "nest" form and shipped in sterile conditions. Shipping syringes in a "nest" format means shipping syringes which have been packaged on a plastic plate mainly comprising a support plate, hereinafter called nest plate, which is formed by a matrix of openings, each of these openings supporting a syringe. This nest plate is typically supported by a plastic box hereinafter called nest box which protects the syringes (see, for example, the product HYPAK® SCF®, Becton, Dickinson and Company of Franklin Lakes, N.J., USA). This packaging is, furthermore, covered by a membrane seal, bagged and then ready for sterilization.

When the syringes are shipped in the "nest" format to a pharmaceutical company, they have to be handled in order to be individually filled. After having removed the bag and the membrane seal from each packaging, manually or by automated equipment means, each nest plate is removed from its corresponding nest box and the syringes are then filled one by one, row by row or by multiple-part series. After the filling step, it is necessary on the one hand to label each syringe in order to define the medical product contained and, on the other hand, to inspect the syringes to detect any contamination of the product as well as any cracks or scratches in the syringes. Other operations may be required such as, for example, the addition of needle protections or plugs. The inspection is conventionally carried out by means of a system of optical sensors (or a camera) which individually inspect the syringes. However, in accordance with the usual practice and because of technical limitations (quantity of syringes, difficulties in labeling and/or inspecting the syringes placed in the central part of the nest plate, etc.), the syringes are first removed from the nest plate before being labeled and/or inspected. Thus, when the syringes are finally labeled and/or inspected, they are then once again handled and stored either directly in the nest box without being stored on the nest plate, or in a different support, hereinafter called comb plate (see the document U.S. Pat. No. 6,012,595 described below). The latter has multiple elongate fingers for keeping the syringes suspended by their collars. It should be noted that, after the labeling and/or inspection, the syringes are no longer reinserted into the nest plate because it is more efficient and easier to store them in the comb plate which is bought separately. A nest-type packaging, such as the product HYPAK®SCF®, is therefore unsuitable for automated handling because it requires complex machinery. Also, in a semi-automatic handling context (with human assistance), it is difficult to exceed rates of more than 6000 syringes per hour. However, while on the one hand the comb plates are preferable to the nest plates for storing the syringes more rapidly and more easily, they are, on the other hand, unsuitable for transporting and storing the syringes. In practice, when the comb plates are stored one on top of the other in vertical columns, some parts of the syringes risk being damaged or broken, because of their direct contact with the underside of the packaging placed above. In order to avoid this problem, the comb plates must be placed in additional specific boxes and provided with lids with an immobilizing internal flange.

Specific boxes in which the medical containers are arranged are known in the art but they are not suited, because of their structure, to all the automated production line steps. Thus, a box that has a structure that is too flexible, i.e. not rigid enough, will, for example, hamper the correct efficiency of a palletization or depalletization step since it will be difficult to handle using an automated system.

Hence, FIG. 1 represents a schematic view of a production line as currently known. This details the different steps undertaken for checking or inspecting vaccine syringes. The quality of the syringe is checked using cameras and optical checkers. The step of the area A corresponds to the movement of a pallet 4 having "nest" boxes filled with syringes. The pallet is brought into an area B by an operator 5 who places the "nest" boxes on an accumulation conveyor 1 supplying the robot 2 of the area C with the boxes. The robot 2 of the area C removes the syringes from the "nest" box to send them to the checking or inspection area D via a new conveyor. At the same time, an operator 6 retrieves the empty "nest" boxes to return them manually to a pallet in area E. The syringes are analyzed by the cameras and/or the optical checkers in the area D then routed into area F where said syringes are arranged on combs and then in boxes and lidded via apparatuses 3. The latter are supplied with combs, boxes and lids by operators 7 who manually route the empty combs, the empty boxes and the lids from the area G to the area F. The last step consists in routing the boxes filled with syringes arranged on the combs and sealed by the lid from the area F to H. The boxes used in the areas F and G and those used in the areas A and B are not the same because of the difficulty in handling nest-type boxes by automated systems at high rate. This production line, usually subject to strict standards of cleanliness and hygiene (Grade A to D, GMP standard) consumes space, consumables, operators and energy because of the problems associated with the overlapping of the boxes in the pallets. Generally, on changes of pallets, the production line has to be stopped, thus creating a stoppage time problem. Grades A and B correspond to a maximum of 3500 particles of 0.5 µm and above per $m^3$ and 0 particles beyond 5 µm. The grade C corresponds to a maximum number of 350,000 particles of 0.5 µm and above per $m^3$ and 2000 particles beyond 5 µm. The grade D corresponds to a maximum number of 3,500,000 particles of 0.5 µm and above per $m^3$ and 20,000 particles beyond 5 µm.

The problems associated with the loading or the unloading of a pallet have not been able to be resolved. Systems comprising a plate between each level of the pallet have been able to be considered but this entails the use of a complex handling clamp device. This palletization or depalletization step is therefore generally performed manually, thus raising all the questions associated with the quality of the products following manual handling: possibility of contamination of the containers, risk of damage linked to the handling, etc.

Obviously, there is, here, a need for a box capable of resolving the limitations and the drawbacks of the current systems and of making it possible to proceed more readily and rapidly with the storage, transportation and delivery of medical containers. There is, in particular, the need for a box which allows vertically-suspended syringes to be supported more easily and more securely, which increases the efficiency and facilitates the handling of large quantities of syringes during the sterilization, filling, labeling and/or inspection procedures, performed by highly automated machines in the production lines.

STATE OF THE ART

The document U.S. Pat. No. 6,012,595 discloses a system for storing syringes. This storage system comprises a box and a plate made of a set of elongate fingers linked to a common edge. These fingers describe a number of parallel channels which support the syringes by their collars. However, this storage system is not capable of supporting the syringes when the plate is removed from the box and turned vertically head downward. Furthermore, this plate requires a specific box that has a lid provided with an immobilizing internal flange for fixing said plate because the channels are not very rigid and can easily be deformed, which may cause syringes to drop and be damaged. Furthermore, this storage system is unsuited to automatic handling at high rates, because it requires the use of a complex automatic machine capable of handling this specific box and this particular plate. Finally, this storage system requires a particular type of plate for a given type of syringe (that is to say, a syringe with a given diameter or a syringe with a given collar type), in order to protect the syringes from being dropped and damaged. The consequence of this is that, to be compatible with the four types of syringes most commonly used, it is necessary to manufacture four different types of storage systems.

This same document U.S. Pat. No. 6,012,595 describes a storage box for syringes (element 50 in FIG. 6(b) of that document) configured to support a comb-shaped plate and having portions for restricting the movement of said plate. Also known from WO 99/45985 (see FIG. 5 of that document) is a box 92 for storing syringes. The box comprises a bottom 96, lower side walls 94 connecting to said bottom, and a step 98 connected to said lower side walls 94. Said box 92 also has upper side walls connected to said step 98 and to a top flange 100. This flange 100 extends over the entire periphery of the top opening of the upper side walls. It allows for the sealing of a sheet 104 for closing the container. However, as represented in FIG. 9a, the presence of this flange 100 means that a box 92 placed on a horizontal surface next to an identical box 92' on a horizontal plane presents a thin edge of the flange 100 alongside the thin edge of the same flange 100' of the other box, so that a slight inequality in the height of the two boxes can result in an overlapping of the two boxes. The thickness of the flange 100 does not eliminate the possibility of overlapping. These storage boxes therefore have handling and storage drawbacks since their configuration does not make it possible to avoid the overlapping with another box of the same type. Furthermore, these boxes do not have means facilitating their automated handling at high rates that is essential in the targeted context.

The aim of the present invention is to provide a box for storing, protecting and transporting objects that have been sterilized or that are to be sterilized which does not have all the disadvantages of the prior art. In particular, the aim of the invention is to propose a box for safely storing, protecting and transporting a large quantity of medical containers and which avoids the overlapping of one box over another during handling, storage or transportation, while allowing the boxes to be arranged one on top of the other. Another aim of the present invention is to provide a box that makes it possible to support the containers in the vertically-suspended and inverted positions. Yet another aim of the present invention is to provide a box which can easily be handled by automated means in order to remove the containers from said devices rapidly and safely. Finally, another aim of the present invention is to provide a box that is compatible with the syringes regardless of their length, type of collar and diameter, for example accepting without distinction syringes of 6.85 mm and of 8.15 mm diameter or having differently shaped flanges.

These days, the packaging for containers of liquid medical products are typically supplied in the form of a block of 1200×1000 mm, pallet format (EuroPallet format), in accordance with the UIC 435-2 standard. This means that several packagings of containers are arranged side by side and one on top of the other. Therefore, another aim of the present invention is to provide a box for storing, protecting and transporting medical containers which is suitable for them to be arranged one beside the other and in columns one on top of the other and protecting said containers from damage or contamination. Another aim of the invention is to provide a container for transporting boxes that makes it possible to support the containers in the vertically suspended and inverted positions. Finally, it is also the aim of the present invention to provide a palletization and depalletization method.

SUMMARY OF THE INVENTION

According to a first aspect of the invention, a box for storing, transporting and protecting vertically-suspended containers is provided. Said box comprises a top opening, a rectangular bottom, lower side walls connecting to said bottom, a step connecting to said lower side walls and forming a bearing for supporting a plate, upper side walls connecting by their bottom end to said step and by their top end to a top flange extending toward the outside of the box. According to the invention, a rim is positioned on the top corners of the box and the upper side walls of the box include at least one portion extending toward the outside of the box, so that said box, when it is positioned side-by-side with a second box, is in contact with said second box via said portion, thus preventing the overlapping of said box with said second box.

According to a first preferred embodiment, said portion is a skirt connected to the top flange.

Said skirt may extend over the entire periphery of the box.

According to a second preferred embodiment, said portion is connected to the step.

Said portion may also extend vertically, substantially vertically, obliquely or in an inverted oblique manner. In this case, the risk of overlapping between two boxes according to the invention positioned side by side is minimal.

Preferably, said at least one portion may be situated in a corner of said box. Preferably, said at least one portion may be situated in a top corner of said box. Advantageously, said box according to the invention may contain four upper side walls each including at least one portion extending outward. Thus, said box may contain at least four portions extending outward. More preferably, said at least four portions can be situated in the top corners of said box.

Preferably, said box may include, in its upper side walls, at least one void for easily grasping and removing said plate from said box. Advantageously, said at least one void may be situated in a corner of said box. Preferably, said at least one void may be situated in a top corner of said box. Said void may contain one or more protuberances, one or more indentations or one or more cavities.

Advantageously, said box may have a parallelepipedal shape.

More advantageously, said box may include perforations in said upper side walls or said lower side walls to facilitate the sterilization of said box and its content. The sterilization of said box and its content may be performed by means of a vapor-sterilization method, by ETO, or by irradiation.

Preferably, said rim may have a concave, convex, rippled, planar shape or any other shape likely to favor and improve its handling by an automatic device. Preferably, said rim is planar.

Preferably, said rim and said top flange connected to one of the upper side walls may include at least one junction point. Advantageously, said rim and said top flange may be approximately in the same plane. Preferably, said rim may extend toward the interior of the box. Alternatively, said rim may extend toward the outside of the box and may include a vertical wall. Said vertical wall may also extend along the top flange.

Preferably, said rim and said top flange may form a continuous surface. Said rim may include, in certain parts, protuberances, irregularities or indentations to favor and improve its handling by an automatic device.

According to a preferred embodiment of the invention, said top flange may have a concave or convex peripheral edge. Preferably, the peripheral edge may be concave. Preferably, said peripheral edge may be situated short of the vertical plane formed by two of said portions. Thus, the contact between boxes according to the invention arranged side by side cannot be made by the peripheral edge of the top flange; a space is then created between two boxes, preventing the overlapping thereof. Alternatively, said portions extend vertically, substantially vertically, obliquely or in inverted oblique manner over all or part of the top flange.

Preferably, said rim and said top flange may be topped by a membrane seal or a lid to favor the stacking of said boxes one on top of the other and limit the exchanges between the interior and the exterior of said boxes. The membrane seal may be made of high density polyethylene fibers, such as Tyvek®. The membrane seal may be glued or welded to said rim and to said top flange.

Preferably, said box may contain a plate to support containers. According to an embodiment of the invention, said plate may be a plate comprising a plurality of rails positioned parallel to one another on one face of said plate, support lips being arranged along said rails, a lip and a rail thus forming, with a lip of an adjacent rail, an opening, a pair of adjacent lips being suitable for supporting and storing containers by their flanges, and in that said plate includes an upper wall perpendicular to said plurality of rails and that said rails and said lips are substantially free of irregularities, thus enabling the containers to slide along the rails. Said plurality of rails may be fixed rigidly to said upper wall so that said openings are not deformed, thus preventing said containers from falling. The plate may thus include secondary rails for preventing the containers from being displaced laterally relative to said openings. The upper wall of said plate may include a plurality of passages formed facing said openings to allow access to an upper face of said containers. Said plate may also include a securing tab configured to receive a plurality of containers by snap-fitting, and to position said objects facing said passages. Furthermore, this type of plate makes it possible to avoid having said containers leave said plate when the latter pivots about a horizontal axis. This plate offers the advantage of being able to be extracted from said box by a sucker system.

According to another embodiment, said plate may be a plate known from the art such as nest plate or a comb-shaped plate.

According to a preferred embodiment, said plate may be topped by at least one protection sheet, sealed or not. The protection sheet may be made of high density polyethylene fibers.

According to a second aspect of the invention, a container for transporting boxes according to the first aspect of the invention is provided. Said container comprises a pallet on which is arranged a plurality of boxes according to the invention and optionally containing a means for checking the quality of said container. Said pallet may be a EuroPallet-type pallet with the standardized dimensions of 800 mm in width by 1200 mm in length. Preferably, said pallet may be a plastic pallet.

According to a preferred embodiment, said container may also include vertical side walls and a rigid lid. The vertical side walls are also known by the term "rigid supporting bands". Said vertical side walls may be made of polyethylene and may be used to hold said plurality of boxes on the pallet while the container is being transported or conveyed. The rigid lid may be used to stack said containers one on top of the other. Said container may also include a cover, one or more straps or a locating deck.

According to a preferred embodiment of the invention, said plurality of boxes may be contained in or surrounded by a protection element. The protection element may be a bag or a package. Preferably, said protection element is configured to maintain said plurality of boxes at a pressure less than atmospheric pressure. The atmospheric pressure considered in the present invention is 1013 hPa. More preferably, said protection element is configured to keep said plurality of boxes in a partial vacuum. The term "partial vacuum" as used in the present invention refers to a pressure below 500 hPa. Said plurality of boxes is then held in a rigid block.

Preferably, said means for checking the quality of said container may be said protection element surrounding said plurality of boxes. Alternatively, said means for checking the quality of said container may be one or more seals, one or more bands, one or more covers, one or more straps, a lid or one or more walls surrounding said container.

According to another aspect, the invention relates to an automatic palletization method, characterized in that it comprises the following steps of:
  providing a plurality of boxes according to the invention and a pallet,
  using an automated device, arranging on said pallet said plurality of boxes according to the invention, side by side or one on top of the other, such that the portions of the upper side walls of said boxes bear against one another preventing them from overlapping,
  supplying a container according to the present invention.

Advantageously, said automated device handles said boxes via their lower side walls, their upper side walls, their voids or by said rims positioned on the top corners of said box.

According to a preferred embodiment of the invention, said automatic palletization method also includes the step of packaging said boxes arranged on the pallet with a protection element. Preferably, said protection element may be a bag or a package. Preferably, said protection element is configured to maintain said plurality of boxes at a pressure lower than atmospheric pressure. More preferentially, said protection element is configured to maintain said plurality of boxes in a partial vacuum. When said protection element is configured to maintain said plurality of boxes in a partial vacuum, the latter acts as a means for checking the quality of said container. In practice, if, when using said container, said plurality of boxes is no longer in a partial vacuum, this implies that the protection element surrounding said boxes is no longer airtight and therefore that said may have been in contact with an external element which may have altered its quality, its sterility. If a number of means for checking the quality have been used, the check can be done at different steps in the procedure. The maintaining of the sterile condition may, for example, be important in the pharmaceutical or medical domain.

According to another preferred embodiment of the invention, said automatic palletization method also includes the step of adding vertical side walls and a rigid lid. Said vertical side walls may be of polyethylene and may be used to hold said plurality of boxes on the pallet while the container is being transported or conveyed. The rigid lid may be used to stack said boxes one on top of the other.

According to another aspect, the invention relates to an automatic depalletization method, characterized in that it comprises the following steps of:
 a) providing a container according to the invention comprising a pallet on which is arranged a plurality of boxes according to the invention,
 b) removing said plurality of boxes from said pallet via an automated system handling said boxes via their lower side walls, their upper side walls 16, their voids or by said rims positioned on the top corners of said box.

According to a preferred embodiment of the invention, said automatic depalletization method also includes a step prior to the step b) of removing said protection element surrounding said plurality of boxes.

According to a preferred embodiment of the invention, said automatic depalletization method also includes a step prior to the step b) of removing the vertical side walls and the rigid lid surrounding said plurality of boxes.

According to another aspect of the invention, the box, according to the first aspect of the invention, is used for storing, transporting and protecting vertically-suspended containers. Preferably, said suspended containers are containers of medical products. More particularly, the containers of medical products may be syringes, flasks or any other object provided with flanges or collars.

Other aspects and advantages of embodiments of the invention will be discussed with reference to the figures and the detailed description of the embodiments.

DETAILED DESCRIPTION OF THE INVENTION

According to a first aspect of the invention, a box for storing, transporting and protecting containers is supplied. Said box comprises a top opening, a rectangular bottom, lower side walls connecting to said bottom, and a step connecting to said lower side walls and forming a bearing to support a plate, characterized in that said box comprises upper side walls connected to said step and each including at least one portion extending toward the outside of the box, each of said upper side walls also being connected to a top flange extending toward the outside of the box, and in that a rim is positioned on the top corners of said box. The box according to the invention makes it possible to avoid and prevent any overlapping with another box of the same type, thus making them easier to handle at a high rate. In practice, the contact between two boxes according to the invention preferably occurs by said portions of the upper side walls so that, even if there is an alignment defect in the vertical plane between said two boxes, no overlapping is observed.

Figure 1:
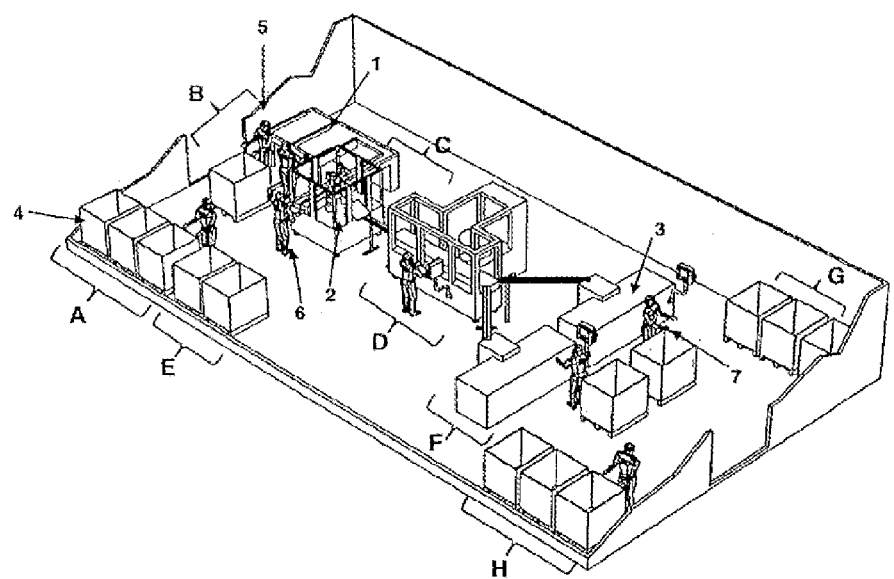
FIG. 1 represents a schematic view of a known production line for checking medical containers.
Figure 2:
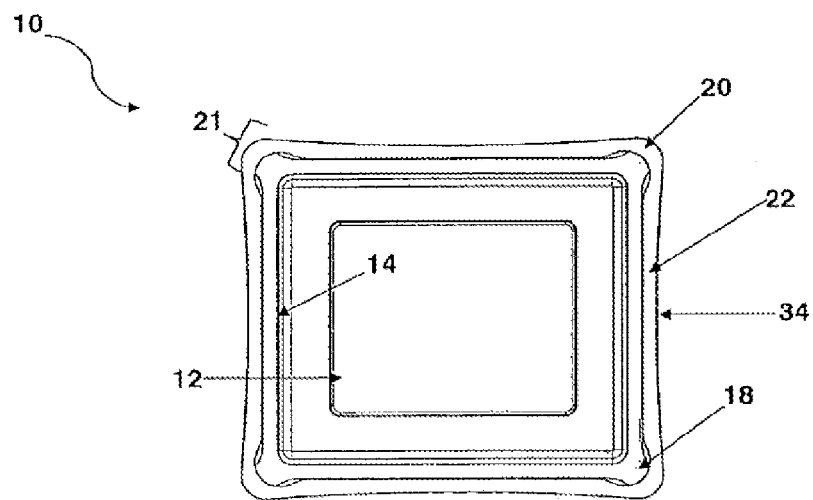
FIG. 2 represents a plan view of a box according to the invention.
Figure 3:
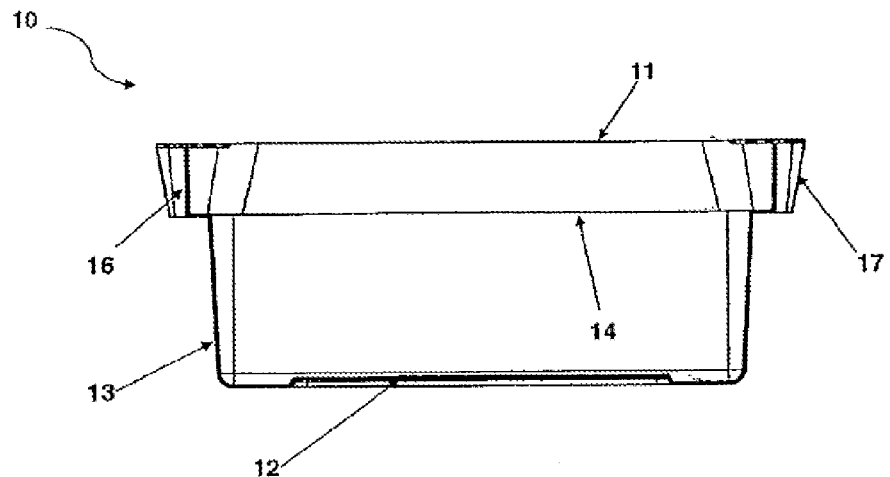
FIG. 3 represents a cross-sectional side view of a box according to the invention.
Figure 4A:
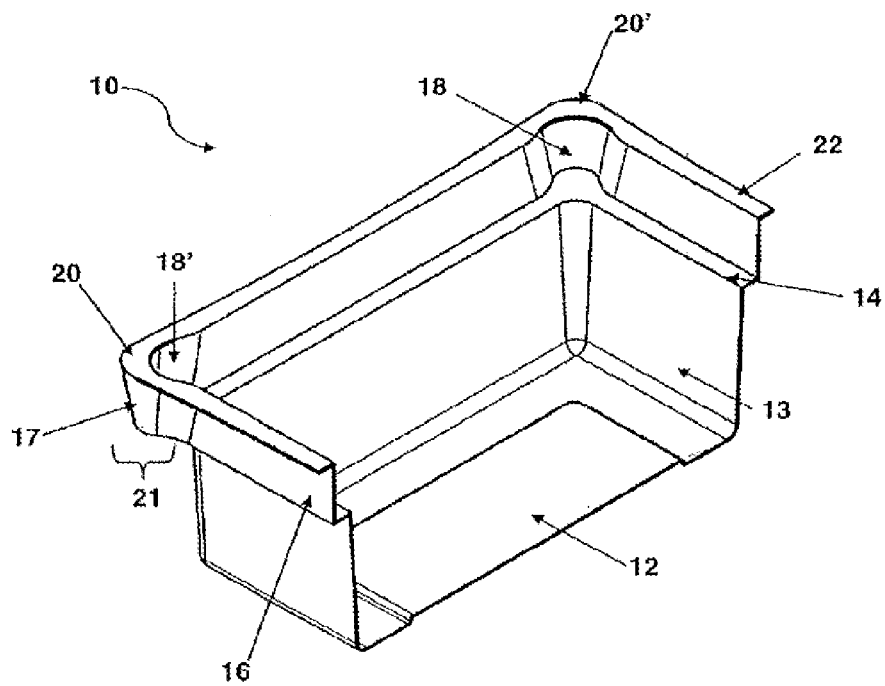
FIG. 4A and 4D represent a cross-sectional perspective view of a box according to the invention.
Figures 4B, 4C:
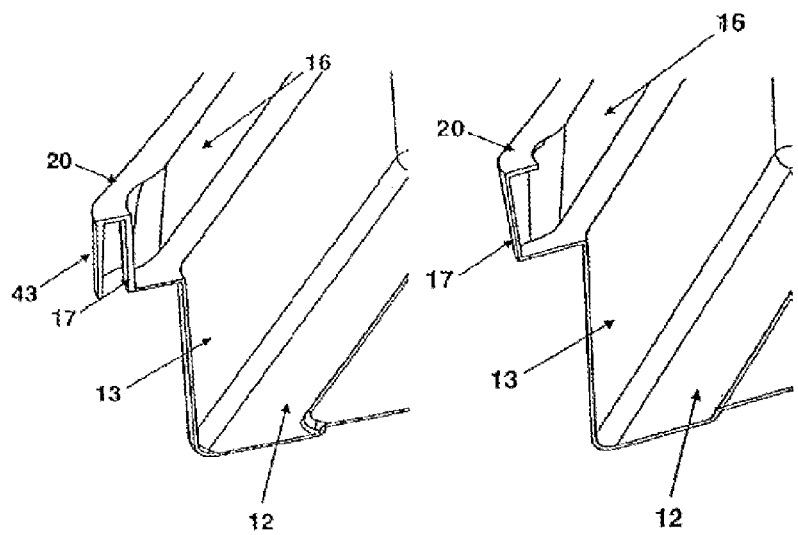
FIGS. 4B and 4C represent a cross-sectional view of a corner of the box according to the invention.

According to this first aspect of the invention, a box for storing, transporting and protecting vertically-suspended containers 28 is provided. FIG. 2 represents a schematic plan view of the box according to a second particular embodiment of the invention. Said box 10 comprises a rectangular bottom 12, lower side walls 13 (not represented in this view) connected to said bottom 12, and a step 14 connected to said lower side walls and forming a bearing to support a plate 15. Said box 10 also includes upper side walls 16 (not represented in this view) and a void 18 at each of its top corners 21. A rim 20 is positioned on each of the top corners of said box 10. Said rims 20 extend towards the interior of the box 10. A top flange 22 is connected to the upper side walls 16, not represented in this view, and has a concave peripheral edge 34. The top flange 22 and said rim 20 form a continuous surface likely to be covered with a membrane seal. Referring to FIG. 3 and FIGS. 4a and 4c, said upper side walls 16 each include at least one, and preferably two, portions 17 extending vertically, obliquely or in an inverted oblique manner toward the outside of the box 10, so that a box 10 can be arranged side by side with another box of the same type in such a way that the portions 17 of these boxes bear on one another leaving spaces 41 between them, as clearly shown in FIG. 5. Said portions 17 extend vertically, obliquely or in an inverted oblique manner, which makes it possible to avoid the overlapping, even when two adjacent boxes 10 are not exactly at the same level. The portions 17 extending toward the outside of the box therefore prevent the top flanges 22 from coming into contact with one another and from overlapping. The boxes known from the prior art, for example from FIG. 6 of U.S. Pat. No. 6,012,595, on the contrary, present thin edges to an adjacent box of the same type, which may result in overlaps if the thin edges of two adjacent boxes do not coincide at the same height.

Said box 10 therefore comprises a top opening 11, a rectangular bottom 12, lower side walls 13 and a step 14 forming a bearing to support a plate. It is in fact important to safeguard the containers 28 from any contact with the box 10. The plate is used to separate syringes, contained in said plate, from the bottom 12 of said box 10. The rectangular bottom 12 may also contain grooves or slots. These may serve to prevent slippage between two surfaces of boxes arranged one on top of the other. In practice, if the top of the plate 15 of a first box includes protuberances, these can be inserted into said slots in the bottom 12.

Referring again to FIG. 2 and FIG. 4A, said box 10 also comprises, in its upper side walls 16, at its four corners, voids 18, 18' to make it possible to easily grasp and remove, when necessary, the plate 15.

Said box also includes a rim 20 positioned on its top corners 21, as illustrated in FIG. 2 and in FIG. 4A, 4B, 4C. Said rim 20 and the top flange 22 form a continuous surface. Said continuous surface is planar and may therefore favor and improve its handling by an automatic device.

Furthermore, when said rim 20 and the top flange 22 form a planar surface, these may be topped with a membrane seal or a lid to favor the stacking of said boxes one on top of the other and limit the exchanges between the interior and the exterior of said box 10.

Referring to FIG. 3, said box 10 comprises a rectangular bottom 12, lower side walls 13 connected to said bottom 12, a step 14 connected to said lower side walls 13, a top opening 11, upper side walls 16 connected to said step 14. Said upper side walls include a portion 17 extending in an inverted oblique manner. Moreover, referring to FIG. 5, the peripheral edge 34 of said top flange 22 connected to an upper side wall 16 is concave. Said peripheral edge 34 does not extend beyond the vertical plane formed by the portions 17 and 17'.

Figure 5:
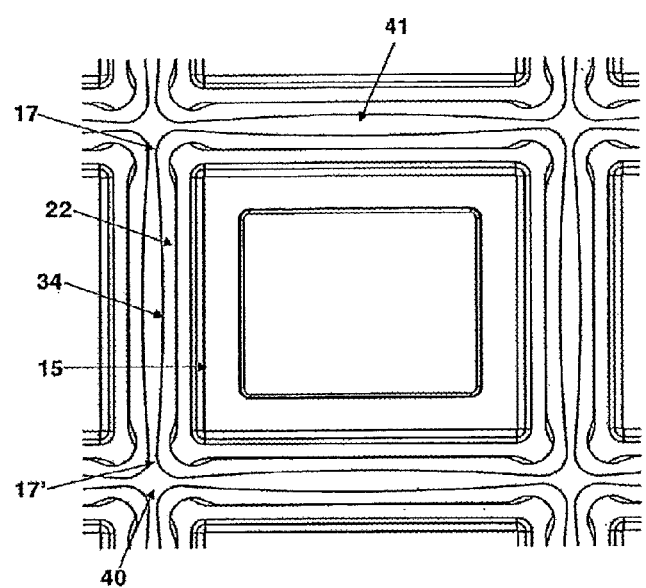
FIG. 5 represents a plan view of a set of boxes according to the invention.
Figure 6:
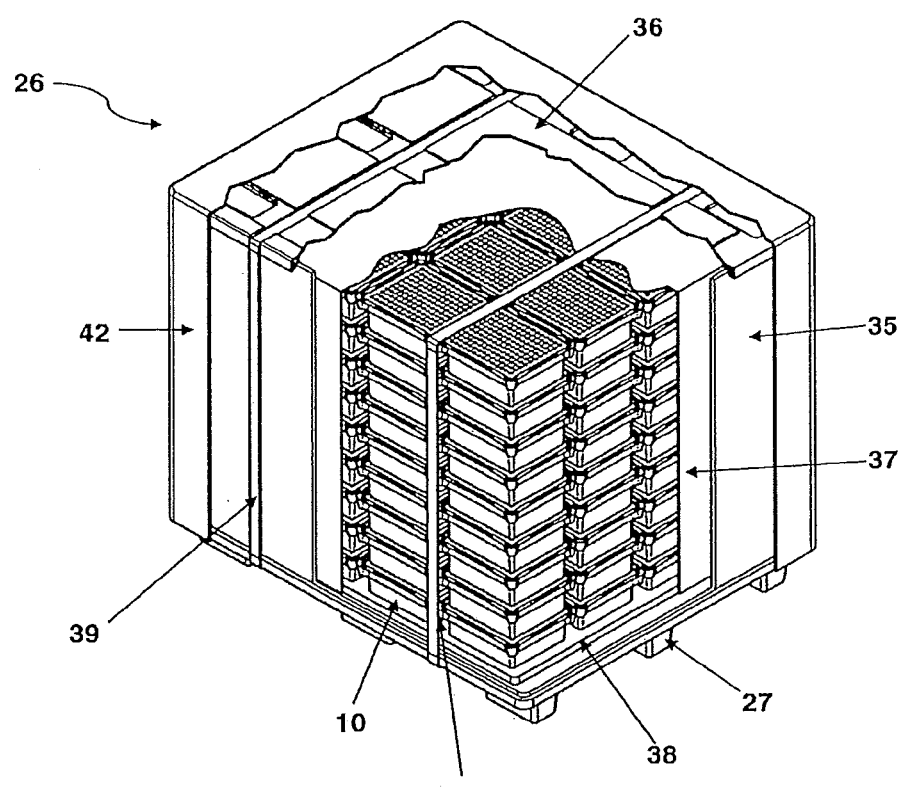
FIG. 6 represents a perspective view of a container according to the invention containing a plurality of boxes according to the invention.

The presence of the spaces 40 and 41 avoids the superposition of boxes 10, which substantially reduces the risk of damaging or breaking stored medical containers even when several boxes are arranged together side by side and/or one on top of the other as shown in FIG. 5 and in FIG. 6.

Figure 4D:
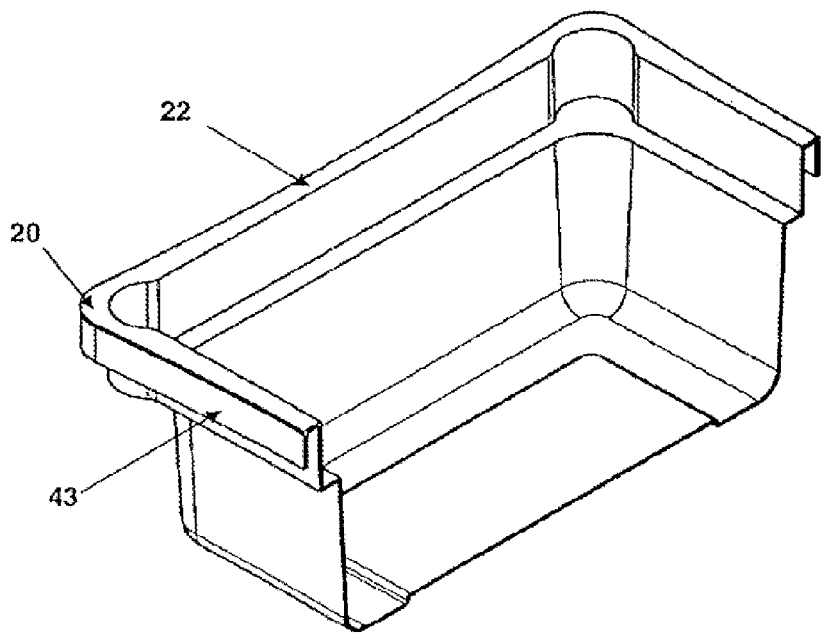

FIG. 4A represents a cross-sectional view of the interior of the box according to the second particular embodiment of the invention. Said box 10 comprises a rectangular bottom 12, lower side walls 13 connected to said bottom 12, a step 14 connected to said lower side walls 13, upper side walls 16 connected to said step 14. A top flange 22 is connected to said upper side walls 16. Furthermore, said box includes voids 18, 18' in the top corners 21. Said top corners 21 are topped with a rim 20 forming a continuous surface with the top flange 22. Said rim 20 extends towards the interior of the box, as represented also in FIG. 4C. The upper side walls 16 each include two portions 17 extending in an inverted oblique manner and situated in the top corners of said box 10. The handling of said box 10 by an automated device is facilitated by the presence of the voids 18 and 18', and of the rims 20 and 20'. FIG. 4B represents a cross-sectional view of a corner of the box 10 according to a first particular embodiment of the invention. Said rim 20 extends toward the outside of the box 10 and includes a vertical wall 43, forming a skirt. In this case, the contact between two boxes may occur via said vertical wall 43. Said vertical wall 43 may also be prolonged along the top edge 22. Said vertical wall 43 may also be prolonged over the entire periphery of the box as represented in FIG. 4D.

Figure 9A:
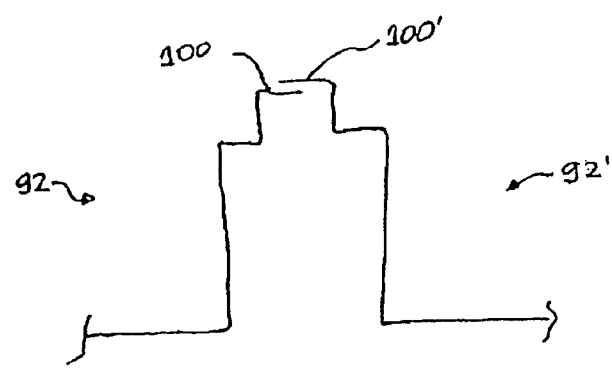
FIG. 9a represents, partially and in cross section, two boxes according to the prior art placed side by side, and likely to overlap.
Figure 9B:
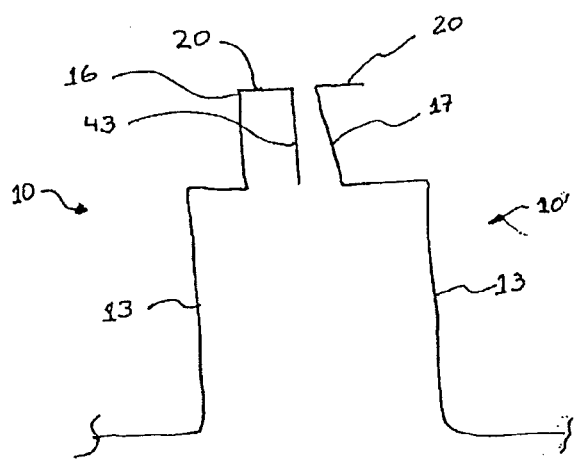
FIG. 9b represents, partially and in cross section, two boxes according to the invention placed side by side.

FIG. 9b represents, partially and in cross section, a box 10 according to a first embodiment of the invention and a box 10' according to a second embodiment of the invention. The skirt 43 of the box 10 extends vertically facing the portion 17 of the box 10' so that, even if there are height inequalities, impacts or vibration during handling and transportation, a box cannot overlap another. FIG. 9b represents the case where the skirt 43 extends vertically and the portion 17 extends in an inverted oblique manner, but it will easily be understood that a skirt 43 or a portion 17 positioned obliquely will have the same effect. Obliqueness angles of 5° to 10° relative to the vertical in one and the other direction are perfectly suitable. It will also be understood that the anti-overlapping effect is obtained as soon as two boxes present to each other a protruding wall with a height greater than the height inequalities and greater than the jumps provoked during transportation and handling.

FIG. 6 is a perspective view showing an arrangement of several boxes 10 of the same type on a pallet 27 (EuroPallet format) side by side and one on top of the other to form a container 26 according to the invention. Said boxes 10 may also be contained in a protection element 28 such as a bag or a package 37. Said container 26 represented in FIG. 6 may optionally include a means for checking the quality of said pallet. If said boxes are contained in a bag or a package 37, said means for checking the quality may make it possible to maintain said object at a pressure lower than atmospheric pressure. This type of arrangement is advantageous for storage, transportation in an industrial installation, or transportation (by road or other means) between two distant industrial installations. Said boxes 10 may contain a plate 15 likely to be used to store medical containers. Said boxes 10 may also be topped with a membrane seal or a lid (not represented in FIG. 6) to favor their stacking and sterility with respect to the outside environment. By virtue of the specific structure of the box 10 according to the invention, said boxes 10 present in the pallet do not overlap. The container 26 may include vertical side walls 35 and a rigid lid 36. As represented in FIG. 6, the container may also include straps 39, a locating deck 38 and a cover 42. Said straps 39, said locating deck 38 and said cover 42 surround or support said plurality of boxes of the container 26 and may also serve as means for checking the quality of said container 26.

Figure 7:
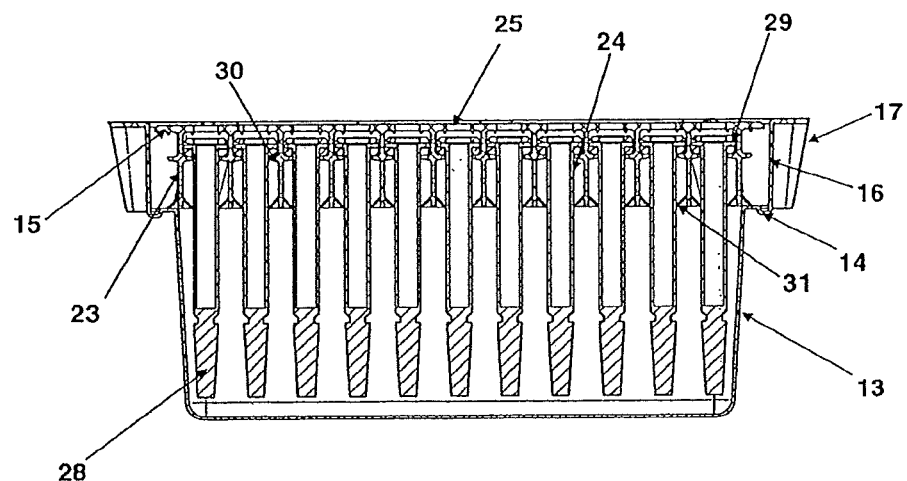
FIG. 7 represents a cross-sectional side view of a box according to the invention containing a plate.

FIG. 7 represents a schematic view of the box according to the invention comprising a plate. Said plate 15 comprises a plurality of rails 23 arranged parallel to one another on one face of said plate. Support lips 30 are arranged along said rails 23, a lip 30 and a rail 23 thus form, with a lip of an adjacent rail, an opening 24, a pair of adjacent lips being able to support and store containers 28 by their flanges 29. Said plate 15 comprises an upper wall 25 perpendicular to said plurality of rails 23. Furthermore, said rails 23 and said lips 30 are substantially free of irregularities, thus enabling the containers 28 to slide along the rails 23. Thus, when a plate 15 is inserted into the box 10 so as to form a sealed packaging, when such a packaging is arranged side by side with another packaging of the same type, the respective portions 17 of each box bear against one another leaving a space 40 between the corners of said boxes 10.

It should be noted that the box according to the invention is totally compatible with the plates of the prior art (such as the nest plates or comb plates).

Figure 8:
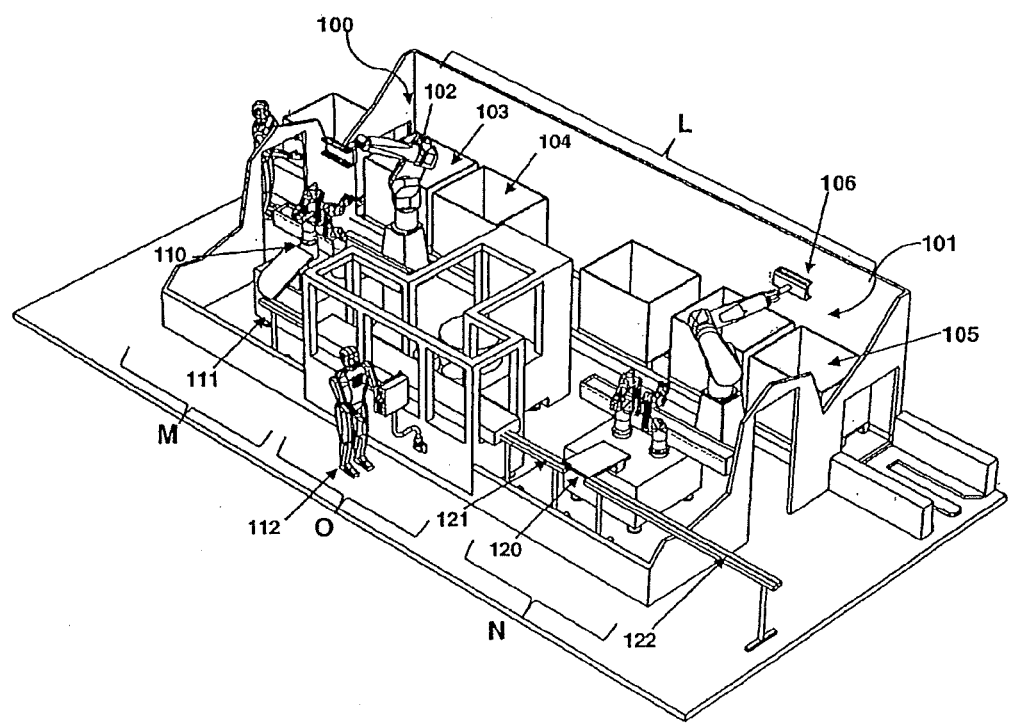
FIG. 8 represents a schematic view of a production line for checking medical containers and using containers and boxes according to the invention.

FIG. 8 represents a production line using boxes and containers according to the invention. The boxes and the containers according to the invention can easily be handled by automated devices by virtue of the configuration of said boxes preventing their overlapping. The production line can therefore be configured, i.e. confined in a closed space, to suit a sterile environment necessary to the produce of vaccines, for example subject to grades A, B, C or D (GMP standard). Such standards impose high and very costly conditions of sterility and cleanliness. Thus, limiting the presence of operators makes it possible to reduce the risks associated with manual handling. Furthermore, the storage and working spaces are significantly reduced, resulting in lower production costs. Thus, the production line may contain several areas: one or more areas intended for conveying the containers, one or more areas for processing the containers and boxes, one or more areas of activity on the containers contained in said boxes. For example, as represented in FIG. 8, the production line may contain an area L for conveying the containers, two areas M and N for processing the containers and the boxes, and an area O of activity on the containers contained in said boxes. In the absence of maintenance or specific work on the production line when stopped, the latter can be isolated from the outside environment in order to preserve the necessary aseptic conditions. The area L may include a system of rails on which the containers according to the invention are conveyed. This area may contain one or more areas for loading or unloading said boxes 10 or said containers 26 according to the invention. For example, said area L may contain a first sub-area 100 in which the containers 103 are unloaded by an automated device 102. For example, said boxes may contain syringes. The boxes (not represented) contained in said container 103 are routed by the device 102 to a first area M for processing said boxes. The area M may contain a device 110 for unloading the syringes stored in said boxes 10 which are subsequently placed on a conveying system 111. Said empty boxes are taken over by the automated system 102 and stored in a container 104. The container 104 will be conveyed in the area L to a second sub-area 101. The syringes unloaded in the processing area M are brought to the area O of activity via the conveying system 111. The activity may be an inspection of the quality of the syringes to assess the presence of defects. Alternatively, the activity may relate to the filling of the syringes with a therapeutic solution such as a vaccine. Alternatively, the activity may also relate to the labeling of the syringes. An operator 112 can intervene in programming and checking the correct progress in the area of activity or the processing areas. Once the activity is completed, the syringes are conveyed to a processing area N via an appropriate conveying system 121. The syringes are, for example, loaded into said boxes (not represented) using an automated system 120. Alternatively, the syringes may be conveyed via a bypass conveyor 122 to another production or assembly line. The box 10 containing the syringes is then placed in a container 105 situated in the area L sub-area 101 using a suitable automated device 106. The containers of the sub-area 101 are then routed to undergo a subsequent processing or to be stored. By virtue of the use of the boxes and containers according to the invention, the production line can be optimized in terms of efficiency, space, rate and quality. The absence of contact between an operator and the medical containers, for example the syringes or flasks, therefore reduces the risks of contamination or damage to said medical containers. The containers and the boxes used in the areas L, M and N are identical and reusable in the production line.

The invention claimed is:

1. Box (10), for storing, transporting and protecting vertically-suspended containers, comprising a top opening (11), a rectangular bottom (12), lower side walls (13) connecting to said bottom (12), a step (14) connecting to said lower side walls (13) and forming a bearing supporting a plate, upper side walls (16) connecting by their bottom end to said step (14) and by their top end to a top flange (22) extending toward the outside of the box (10), wherein a rim (20) is positioned on the top corners (21) of said box (10) and in that said upper side walls (16) of said box (10) include at least one portion (17; 43) extending toward the outside of the box (10), so that said box (10), when it is positioned side-by-side with a second box (10), is in contact with said second box via said at least one portion (17, 43) thus preventing the overlapping of said box with said second box, and wherein said at least one portion (17: 43) extends vertically, obliquely or in an inverted oblique manner.

2. Box according to claim 1, wherein said at least one portion (17; 43) is a skirt (43) connected to the top flange (22).

3. Box according to claim 2, wherein said skirt (43) extends over the entire periphery of the box.

4. Box according to claim 1, wherein said at least one portion (17) is connected to the step (14).

5. Box according to claim 1, wherein said at least one portion (17; 43) is located in a corner of said box (10).

6. Box according to claim 1, wherein it comprises, in its upper side walls (16) at least one void (18) for easily grasping and removing a plate (15) from said box (10).

7. Box according to claim 6, wherein said at least one void (18) is situated in a corner of said box (10).

8. Box according to claim 1, wherein said box (10) has a parallelepipedal shape.

9. Box (10), for storing, transporting and protecting vertically-suspended containers, comprising a top opening (11), a rectangular bottom (12), lower side walls (13) connecting to said bottom (12), a step (14) connecting to said lower side walls (13) and forming a bearing supporting a plate, upper side walls (16) connecting by their bottom end to said step (14) and by their end to a top flange (22) extending toward the outside of the box (10), wherein a rim (20) is positioned on the top corners (21) of said box (10) and in that upper side wall (16) of said box (10) include at least one portion (17; 43) extending toward the outside of the box (10), so that said box (10), when it is positioned side-by-side with a second box (10), is in contact with said second box via said at least one portion (17, 43) thus preventing the overlapping of said box with said second box, wherein said rim (20) includes at least one junction point with said top flange (22).

10. Box according to claim 1, wherein said rim (20) and said top flange (22) are approximately in the same plane.

11. Box according to claim 1, wherein said rim (20) extends towards the interior of the box.

12. Box (10), for storing, transporting and protecting vertically-suspended containers, comprising a top opening (11), a rectangular bottom (12), lower side walls (13) connecting to said bottom (12), a step (14) connecting to said lower side walls (13) and forming a bearing supporting a plate, upper side walls (16) connecting by their bottom end to said step (14) and by their end to a top flange (22) extending toward the outside of the box (10), Wherein a rim (20) is positioned on the top corners (21) of said box (10) and in that upper side wall (16) of said box (10) include at least one portion (17; 43) extending toward the outside of the box (10), so that said box (10), when it is positioned side-by-side with a second box (10), is in contact with said second box via said at least one portion (17, 43) thus preventing the overlapping of said box with said second box, wherein said rim (20) and said top flange (22) from a continuous surface.

13. Box according to claim 1, wherein said rim (20) and said top flange (22) are topped by a membrane seal or a lid to favor the stacking of said boxes one on top of the other and limit the exchanges between the interior and the exterior of said box (10).

14. Box according to claim 1, wherein said top flange (22) has a concave peripheral edge (34).

15. Box according to claim 14, wherein said peripheral edge (34) is situated short of the vertical plane formed by two of said portions (17; 43).

16. Box according to claim 15, wherein said vertical wall extends over the entire periphery of said box (10).

17. Box according to claim 1, wherein it comprises a plate (15), said plate (15) including a plurality of rails (23) positioned parallel to one another on one face of said plate, support lips (30) being arranged along said rails (23), a lip (30) and a rail (23) thus forming, with a lip of an adjacent rail, an opening (24), a pair of adjacent lips being suitable for supporting and storing containers (28) by their flanges (29), and in that said plate (15) includes an upper wall (25) perpendicular to said plurality of rails (23) and that said rails and said lips are substantially free of irregularities, thus enabling the containers (28) to slide along the rails (23).

18. Box according to claim 1, wherein it comprises a plate (15), said plate (15) being comb-shaped or a plate of nest type.

* * * * *